United States Patent

Simon et al.

[11] Patent Number: 5,836,968
[45] Date of Patent: Nov. 17, 1998

[54] REMOVABLE EMBOLUS BLOOD CLOT FILTER

[75] Inventors: Morris Simon, Boston; Stephen J. Kleshinski, Scituate; Thomas F. Kinst, Chelsea, all of Mass.

[73] Assignee: Nitinol Medical Technologies, Inc., Boston, Mass.

[21] Appl. No.: 896,964

[22] Filed: Jul. 16, 1997

Related U.S. Application Data

[62] Division of Ser. No. 682,192, Jul. 17, 1996, Pat. No. 5,669,933.

[51] Int. Cl.⁶ .................................................. A61M 29/00
[52] U.S. Cl. ............................................. 606/200; 606/198
[58] Field of Search ................................ 606/1, 191–200; 623/1, 11, 12

[56] References Cited

U.S. PATENT DOCUMENTS 5,370,657  12/1994  Irie .......................................... 606/200
5,634,942  6/1997  Chevillon et al. ........................ 606/200
5,669,933  9/1997  Simon et al. ............................. 606/200

*Primary Examiner*—Glenn K. Dawson
*Attorney, Agent, or Firm*—Sixbey, Friedman, Leedom & Ferguson; Daniel W. Sixbey

[57] ABSTRACT

A blood clot filter which is collapsible toward a central longitudinal axis into a collapsed configuration for insertion into a blood vessel and which is radially expandable outwardly from the longitudinal axis to an expanded configuration for contact with the inner wall of the blood vessel at two longitudinally spaced locations. A first plurality of spaced, elongate arms, in the expanded configuration of the filter, curve outwardly away from the longitudinal axis toward the trailing end of the filter to form a first filter basket. These arms prevent movement of the filter in a first longitudinal direction. A second plurality of spaced elongate legs angle outwardly away from the longitudinal axis toward the leading edge of the filter in the expanded configuration thereof. These second legs form a second filter basket opening toward the leading end and prevent longitudinal movement of the filter in a second direction opposite to the first direction.

19 Claims, 3 Drawing Sheets

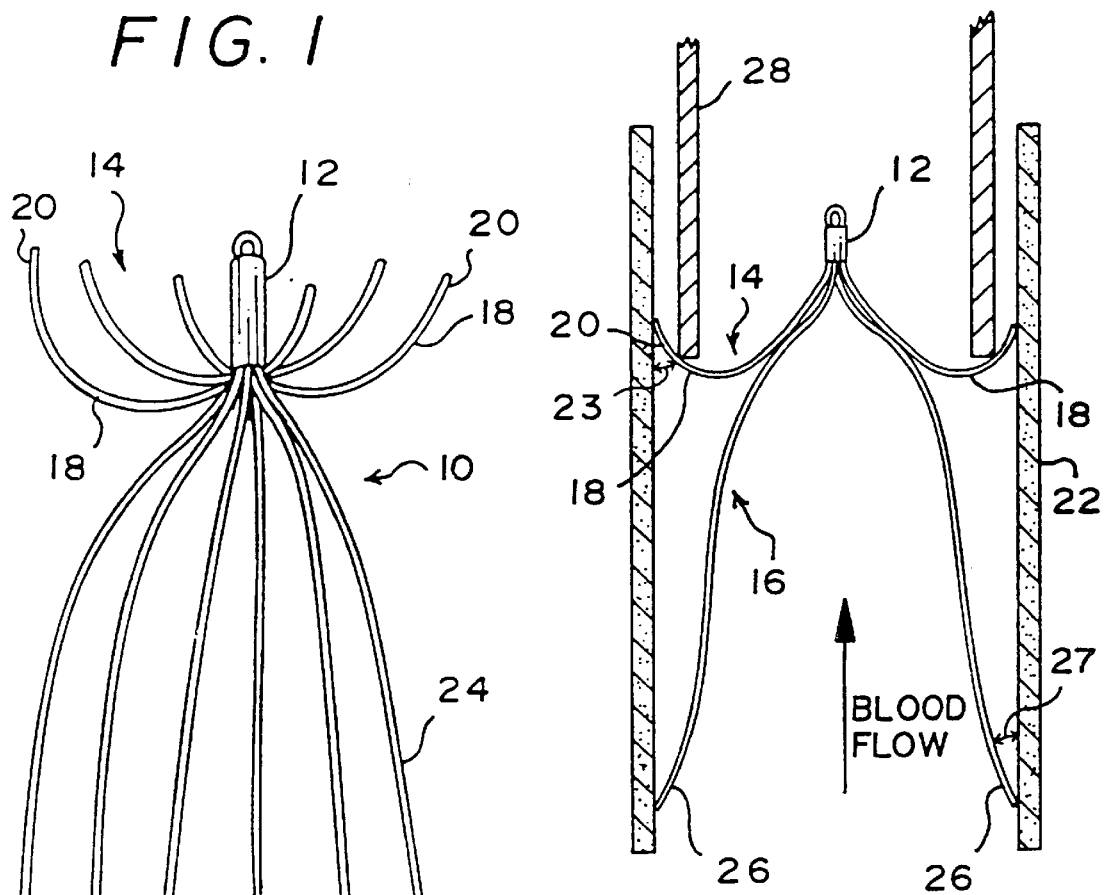
FIG. 1
FIG. 2
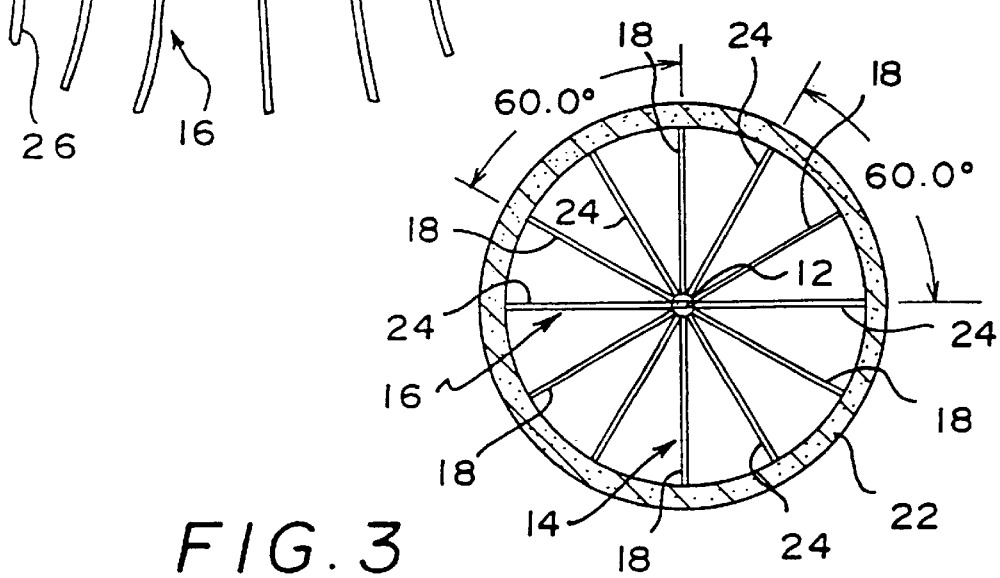
FIG. 3

REMOVABLE EMBOLUS BLOOD CLOT FILTER

This is a Divisional application of Ser. No. 08/682,192, filed Jul. 17, 1996, now U.S. Pat. No. 5,669,933.

BACKGROUND OF THE INVENTION

In recent years, a number of medical devices have been designed which are adapted for compression into a small size to facilitate introduction into vascular passageway and which are subsequently expandable into contact with the walls of the passageway. These devices, among others, include blood clot filters which expand and are held in position by engagement with the inner wall of a vein. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed and fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature level and thereby softened for loading into a catheter in a relatively compressed and elongated state, and to regain the memorized shape in an austenitic state when warmed to a selected temperature, above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

U.S. Pat. No. 4,425,908 to Simon discloses a very effective blood clot filter formed of thermal shape memory material. This filter, like most previously developed vena cava filters, is a permanent filter which, when once implanted, is designed to remain in place. Such filters include structure to anchor the filter in place within the vena cava, such as elongate diverging legs with hooked ends that penetrate the vessel wall and positively prevent migration in either direction longitudinally of the vessel. Within two to six weeks after a filter of this type has been implanted, the endothelium layer grows over the diverging legs and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often adverse to receiving a permanent implant, for the risk of pulmonary embolism may disappear after a period of several weeks or months. However, most existing filters are not easily or safely removable after they have remained in place for more than two weeks, and consequently longer term temporary filters which do not result in the likelihood of injury to the vessel wall upon removal are not available.

In an attempt to provide a removable filter, two filter baskets have been formed along a central hub which are conical in configuration, with each basket being formed by spaced struts radiating outwardly from a central hub. The central hubs are held apart by a compression unit, and the arms of the two baskets overlap so that the baskets face one another. Devices of this type require the use of two removal devices inserted at each end of the filter to draw the baskets apart and fracture the compression unit. The end sections of the arms are formed to lie in substantially parallel relationship to the vessel wall and the tips are inclined inwardly to preclude vessel wall penetration. If a device of this type is withdrawn before the endothelium layer grows over the arms, vessel wall damage is minimized. However, after growth of the endothelium layer the combined inward and longitudinal movement of the filter sections as they are drawn apart can tear this layer. U.S. Pat. No. 5,370,657 to Irie is illustrative of a prior art removable filter requiring two removal devices.

SUMMARY OF THE INVENTION

It is a primary object of the present invention to provide a vessel implantable filter of shape memory material having temperature induced austenitic and martensite states which may be easily removed by a single removable device after an extended period of time without injuring the vessel wall.

Another object of the present invention is to provide a blood clot filter of Nitinol which operates in a temperature induced austenitic state to exert a force on the walls of a vessel by means of oppositely disposed legs to maintain the filter in place, but which may easily be removed after the endothelium layer has covered the ends of the filter legs.

A further object of the present invention is to provide a novel and improved filter of shape memory material having a first group of arms and second group of legs which initially incline in the same direction from a central axis. The ends of the arms in the first group of arms are oriented to engage a vessel wall to prevent longitudinal movement of the filter along the vessel in a first direction, and the ends of the legs of the second group of legs are oppositely oriented to engage the vessel wall to prevent longitudinal movement of the filter along the vessel in a second opposite direction. The ends of both groups of arms and legs are configured to permit withdrawal from the endothelium layer without risk of injury to the vessel wall.

A still further object of the present invention is to provide a novel and improved filter of shape memory material designed to facilitate removal of the filter from a vessel by a two stage removal process accomplished at one end of the filter.

According to the invention, a resilient, longitudinally extended blood clot filter is inwardly radially collapsible toward its longitudinal axis into a collapsed configuration for insertion into a vein, but is adapted for automatic radial expansion into contact with the inner wall of the vein at two longitudinally spaced peripheral locations therein. The filter has leading and trailing ends and comprises a plurality of wires. The wires, in the normal expanded configuration of the filter, are in the form of a plurality of elongated arms and legs with openings between the wires providing filter baskets at the leading and trailing ends of the filter. The wires have peripheral portions for contact with the inner wall of the vein at two longitudinally spaced peripheral locations.

To provide a filter that is inwardly radially collapsible from its normally expanded configuration toward its longitudinal axis into a collapsed configuration for insertion into a vein, the blood clot filter is preferably formed from a plurality of wire portions composed of a shape memory material having a first, low-temperature condition and a second, high-temperature condition. The material in its low-temperature condition is relatively pliable (so that the wire portions may be straightened) and in its high-temperature condition is resiliently deformable and relatively rigid, and takes a pre-determined functional form.

In the high-temperature condition of the material, the filter comprises coaxial first and second filter baskets, each filter basket being generally symmetrical about the longitudinal axis of the filter with one filter basket being concave and one being at least partially convex relative to the filter leading end.

BRIEF DESCRIPTION OF THE DRAWINGS

FIG. 1 is a side view of an expanded blood clot filter of the present invention;

FIG. 2 is a diagrammatic view of the filter of FIG. 1 in place within a vessel;

FIG. 3 is a diagrammatic plan view of the filter of FIG. 1 in place within a vessel;

FIG. 7 is a partially sectional cutaway view of a removal tool for the blood clot filter of the present invention.

DETAILED DESCRIPTION

Figure 4:
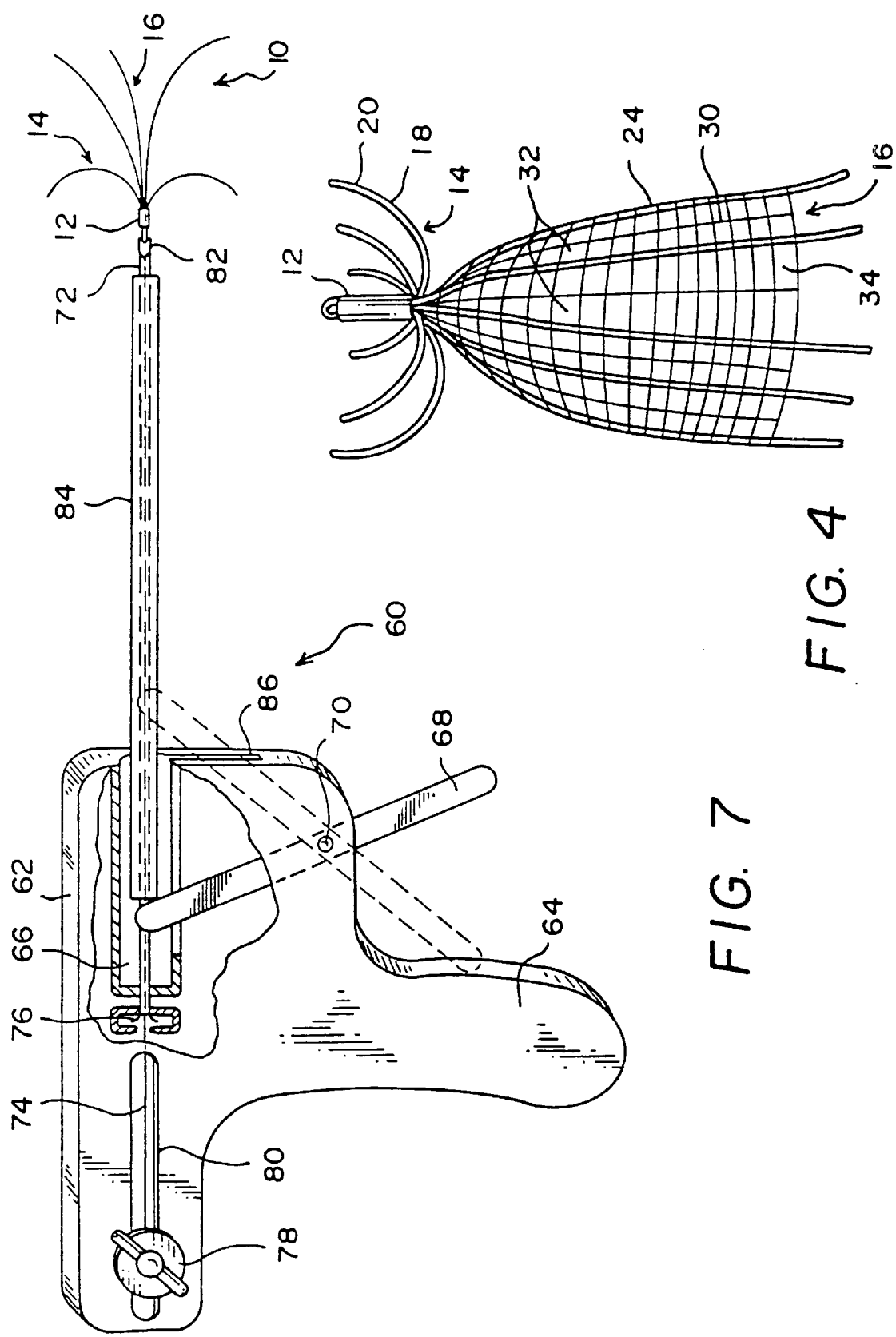
FIG. 4 is a side view of a second embodiment of the blood clot filter of the present invention.

By forming the body of a blood clot filter of a Nitinol alloy material, such as Nitinol wire, transition between the martensitic and austenitic states of the material can be achieved by temperature transitions above and below a transition temperature or transition temperature range which is at or below body temperature. Such controlled temperature transitions have conventionally been employed to soften and contract the Nitinol filter body to facilitate insertion into a catheter and to subsequently expand and rigidify the body within a vascular or other passageway. Although the filters of the present invention are preferably formed from a temperature responsive shape memory material, such as Nitinol, they can also be formed of a compressible spring metal such as stainless steel or a suitable plastic.

Referring now to FIGS. 1 and 2, an expanded blood clot filter 10 is illustrated which is made from sets of elongate metal wires. The wires are held together at one end at a hub 12 where they are spot welded together or otherwise joined. In the low temperature martensite phase of wires made of shape memory material, the sets of wires can be straightened and held in a straight form that can pass through a length of fine plastic tubing with an internal diameter of approximately 2 mm (#8 French catheter). In its high temperature austenitic form, the filter 10 recovers a preformed filtering shape as illustrated by FIG. 1. Similarly, wires of spring metal can be straightened and compressed within a catheter or tube and will diverge into the filter shape of FIG. 1 when the tube is removed.

In its normal expanded configuration or preformed filtering shape, filter 10 is a double filter, having a first filter basket section 14 and a second oppositely disposed filter basket section 16. The two filter sections provide peripheral portions which engage the inner wall of the vein at two longitudinally spaced locations and, the two basket filter sections are generally symmetrical about a longitudinal axis passing through the hub 12.

The first filter basket section 14 is formed from short, arcuate lengths of wire 18 which form arms that curve downwardly, outwardly and upwardly from the hub 12 toward the trailing end of the filter 10. The tip sections 20 of the wires 18 are substantially straight lengths with ends which lie on a circle at their maximum divergence and the tip sections engage the wall 22 of a vessel at a slight angle 23 (preferably within a range of from ten to forty-five degrees) to anchor the filter 10 against upward movement in FIG. 2. Normally, there are six wires 18 of equal length extending radially outward form the hub 12 and circumferentially spaced, such as for example by sixty degrees of arc as shown in FIG. 3.

The second filter basket section 16 is oppositely oriented relative to the first filter basket section 14, and normally includes six circumferentially spaced wires 24 forming downwardly extending legs which tilt and bow outwardly of the longitudinal axis of the filter 10 from the hub 12. The wires 24 are of equal length and are preferably much longer than the wires 18, and have tip sections 26 which are substantially straight lengths with ends which lie on a circle at their maximum divergence. As shown in FIG. 2, the tip sections 26 engage the vessel wall 22 at a slight angle 27, preferably within a range of from ten to forty-five degrees, to anchor the filter against downward movement in FIG. 2. As will be noted in FIG. 3, the wires 24 are radially offset relative to the wires 18 and may be positioned halfway between the wires 18 and also may be circumferentially spaced by sixty degrees of arc. Thus the combined filter basket sections 14 and 16 can provide a wire positioned at every thirty degrees of arc at the maximum divergence of the filter sections. With reference to the direction of blood flow in FIG. 2, the filter section 14 forms a convex filter basket opening toward the trailing end of the filter 10 while the filter section 16 forms a concave filter basket opening toward the leading end of the filter 10.

After the filter 10 has remained in place within a vessel for a period of time in excess of two weeks, the endothelium layer will grow over the tip sections 20 and 26. However, since these tip sections are substantially straight sections of wire oriented at a small angle to the vessel wall 22, the filter can be removed leaving only twelve pin point lesions in the surface of the endothelium. To accomplish this, a catheter or similar tubular unit 28 is inserted over the hub 12 and into engagement with the arms 18. While the hub 12 is held stationary, the catheter is moved downwardly in FIG. 2 forcing the arms 18 downwardly and thereby withdrawing the tip sections 20 from the endothelium layer. Then the hub 12 is drawn into the catheter to withdraw the tip sections 26 from the endothelium layer and collapse the entire filter 10 within the catheter. When the filter is formed from shape memory material, cooling fluid can be passed through the catheter to aid in collapsing the filter. It is important to first disengage the wires 18 by downward movement of the catheter but not to engage the wires 24, for the catheter would force the legs 24 inwardly causing the tips 26 to move inwardly tearing the vessel wall. Once the arm tips 20 are disengaged, the catheter is held stationary and the filter is pulled upwardly into the catheter.

FIG. 4 illustrates a second embodiment of the blood clot filter of the present invention wherein elements having the same structural configuration and operation as those shown in FIGS. 1–3 are designated with the same reference numerals.

In the filter of FIG. 4, a flexible mesh 30 is engaged with the wires 24 of the second filter basket section 16 to expand and contract therewith. The mesh strands may be secured to the wires 24 or the mesh, which forms a pocket 32 with an open end 34, may surround the wires 24 and be attached to the hub 12. The mesh 30 will permit blood to pass through the section 16 but will capture bone chips and small particles which might otherwise pass between the wires 24 and 18. As the filter is withdrawn collapsing the section 16, the mesh is collapsed around particles contained therein which are then withdrawn with the filter.

Figure 5:
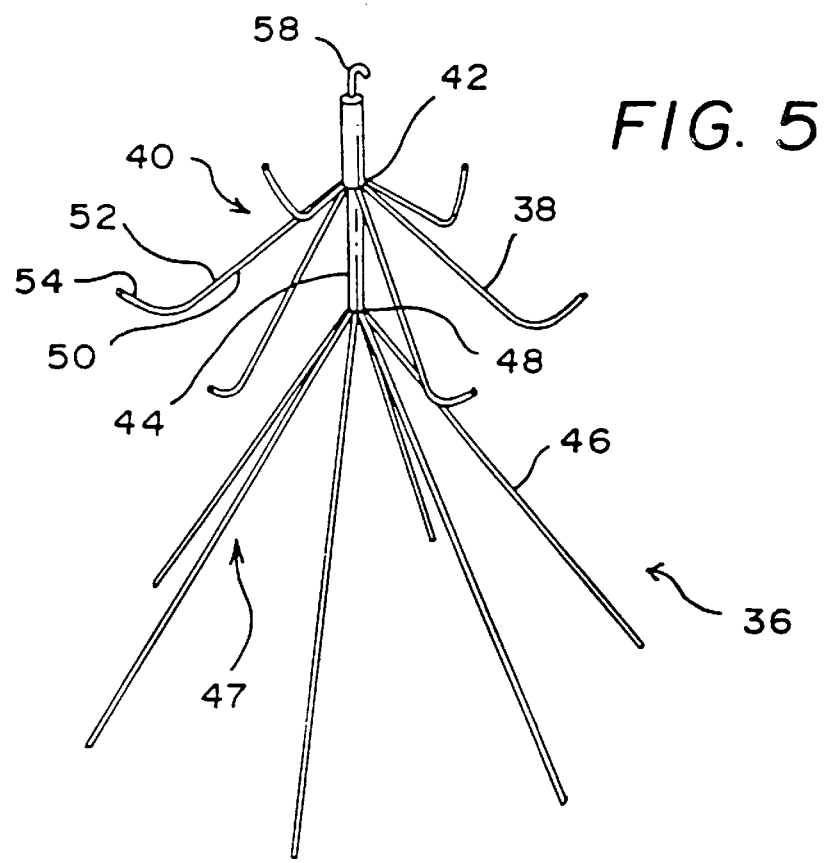
FIG. 5 is a side view of a third embodiment of the blood clot filter of the present invention.
Figure 6:
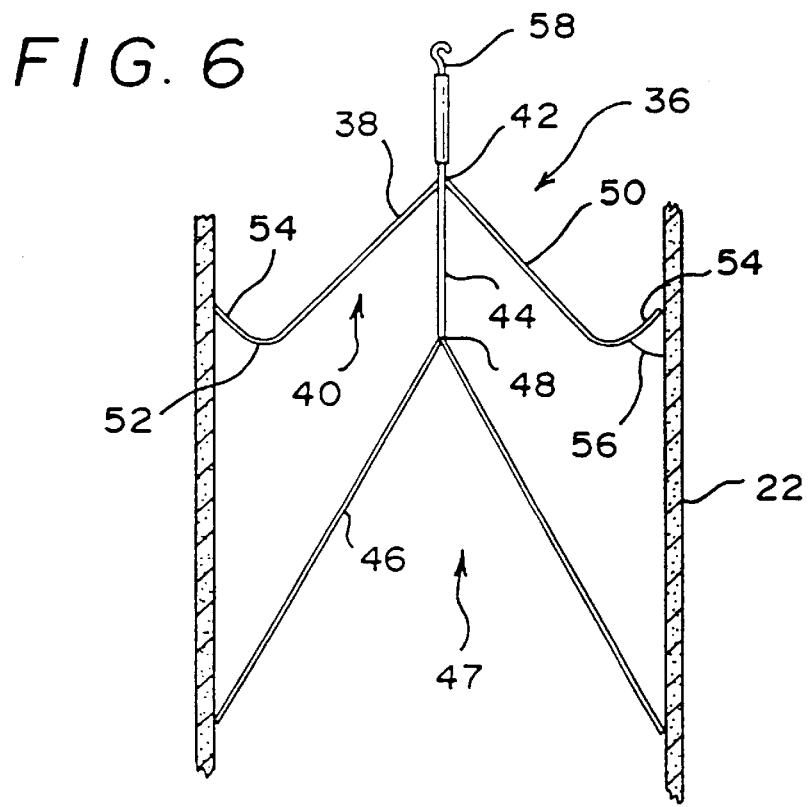
FIG. 6 is a diagrammatic view of the filter of FIG. 5 in place within a vessel.

With reference to FIGS. 5 and 6, a third embodiment of the blood clot filter is indicated generally at 36. Here, the wire arms 38 of a first filter basket 40 extend outwardly from a first juncture 42 on a central shaft 44 and the straight wire legs 46 of a second filter basket 47 extend outwardly from a second juncture 48 on the central shaft spaced below the first juncture. It should be noted that initially the shorter arms 38 extend from the first juncture 42 in an angular direction relative to the central shaft 44 which is the same angular direction that the longer legs 46 extend from the second juncture 48. In fact, the arms and legs may extend from the first and second junctures at the same angle; i.e. an angle of up to 70 degrees. These shorter arms have extended straight sections 50 which extend angularly out from the juncture 42 to form the first filter basket which throughout substantially its extent is coextensive but spaced from the second filter basket 47 formed by the legs 46. At the ends of the straight sections are elbows 52 which join a vessel wall engaging section 54. The wall engaging sections 54 are substantially straight lengths of wire which engage the vessel wall 22 at an angle 56 within a range of from ten to ninety degrees.

To remove the blood clot filter 36, a removal wire or rod is engaged with a hook 58 at the end of the central shaft 44 to hold the filter in place while a catheter or removal tube is moved into engagement with the arms 38 over the hook. The catheter is moved downwardly until the wall engaging sections 54 are withdrawn from the endothelium layer and the vessel wall 22. The angle of the wall engaging sections combined with the angle of the straight sections 50 causes the wall engaging sections to move downwardly and outwardly from the endothelium layer without tearing the vessel wall.

It is important that the catheter or removal tube not contact the legs 46, as inward movement of these legs, when encased by the endothelium layer would be likely to damage the vessel wall. Once the arms 38 are disengaged from the vessel wall, the hook 58 is drawn into the catheter or removal tube to draw the legs 46 upwardly out of the endothelium layer and into the catheter or removal tube.

The blood clot filter 36, like the blood clot filter 10, may be formed of spring metal or plastic, but is preferably formed of shape memory material as previously described. In the case of both filters, it is possible to have the first filter basket expand at a different transition temperature than that of the second filter basket by annealing the wires of the respective filter baskets differently to set different transition temperatures. This may also be achieved by making the wires of one filter basket thicker or greater in cross section than those of the remaining filter basket, at least in some section along the length of the wires.

FIG. 7 illustrates a removal device 60 for removing the blood clot filters 10 and 36 of the present invention. This removal device includes a housing 62 from which a handle 64 projects. An open ended chamber 66 is formed in the front portion of the housing 62 and a trigger 68 pivoted to the housing at 70 projects into the chamber 66. Extending through the chamber is a tubular cover 72 for a snare wire 74 and this cover is secured at 76 to the housing 62 so that the cover is restrained against longitudinal movement. One end of the snare wire is connected to a snare lock 78 which may be variably positioned in a slot 80 in the housing, and the opposite end of the snare wire projects from the tubular cover 72 and includes a hook or other snare device 82 for engagement with the hook 58 or the hub 12 of a filter. A filter removal tube or sheath 84 is inserted over the cover 72 and into the chamber 66 until it contacts the end of the trigger 68.

To remove a filter, the removal tube is inserted into close proximity with the hub 12 or hook 58, and the snare wire is moved longitudinally until the snare device 82 engages the hub or hook. With the snare device engaged, the snare lock 78 is tightened to lock the snare wire against longitudinal movement. Now the trigger 68 is pivoted to the dotted line position in FIG. 7 to move the removal tube longitudinally out of the chamber 66 while the snare wire holds the filter against movement. The trigger moves to the extended dotted line position through a slot 86 in the housing, and the trigger is designed so that the distance travelled between the retracted solid line position of the trigger and the extended position moves the extraction tube over the filter for a distance sufficient to disengage the filter arms but not sufficient to bring the extraction tube into contact with the filter legs. The trigger mechanism can be designed to vary the distance that the extraction tube travels to accommodate different filter sizes, such as example by altering the position of the pivot point 70.

Once the arms of the filter have been disengaged, the extraction tube is manually grasped to hold it stationary while the handle 64 is moved to the left in FIG. 7 to disengage the filter legs and draw the filter into the extraction tube. Thus the basic method for removal of the filter is to first grasp the trailing end and hold the filter against longitudinal movement. Then, while the filter is held stationary, an extraction tube is moved over the trailing end and into contact with the arms of the filter. The extraction tube is moved longitudinally toward the leading end of the filter for a distance sufficient to disengage the filter arms from the vessel wall while preventing engagement of the extraction tube with the filter legs. Finally, the filter is moved longitudinally toward the trailing end to disengage the filter legs from the vessel wall. The housing 62 may be provided with an infusion opening so that cooling fluid can be delivered through either the extraction tube 84 or the tubular cover 72 to aid in the extraction of the filter.

The filter may be positioned initially within a vessel by known delivery devices such as the one shown in U.S. Pat. No. 4,425,908 to Morris Simon.

We claim:

1. A blood clot filter having a central longitudinal axis which is collapsible into a collapsed configuration toward said longitudinal axis for insertion into a blood vessel and which is radially expansible outwardly from said longitudinal axis to an expanded configuration for contact with an inner wall of said blood vessel at two longitudinally spaced locations, said blood clot filter having leading and trailing ends and comprising:

a first plurality of spaced wires which, in the expanded configuration of said filter extend outwardly away from said longitudinal axis toward the leading end and bend back to form a first filter basket opening towards the trailing end; and a second plurality of spaced wires which, in the expanded configuration of said filter angle outwardly away from said longitudinal axis toward the leading end of said blood clot filter to form a second filter basket opening toward said leading end, and a central shaft extending along said central longitudinal axis, said first plurality of spaced wires forming elongate arms having first ends connected to said shaft at a first juncture therewith, and said second plurality of spaced wires forming elongate legs having first ends connected to said shaft at a second juncture spaced from said first juncture, said first and second junctures being fixed in position on said shaft.

2. The blood clot filter of claim 1 wherein said elongate arms extend outwardly at 60 degree intervals from said longitudinal axis and said elongate legs extend outwardly at 60 degree intervals from said longitudinal axis.

3. The blood clot filter of claim 1 which includes a connector mounted above said first filter basket and wherein said first and second filter baskets are generally symmetrical about said longitudinal axis which passes longitudinally through said connector.

4. The blood clot filter of claim 1 wherein said elongate arms and elongate legs are formed of thermal shape memory material having a temperature transformation level below which said material is relatively pliable and compressible and above which said material is self-expandable to a substantially rigid predetermined configuration.

5. The blood clot filter of claim 4 wherein said elongate arms and elongate legs are formed of Nitinol.

6. The blood clot filter of claim 4 wherein said temperature transformation level is at or below body temperature.

7. The blood clot filter of claim 1 wherein said elongate arms are connected against longitudinal movement along said shaft at said first juncture and said elongate legs are connected against longitudinal movement along said shaft at said second juncture.

8. The blood clot filter of claim 1 wherein said elongate arms each include an elongate, substantially straight first section extending angularly outward toward said leading end from said first juncture, an elbow at the end of said substantially straight first section shaped to extend laterally from said straight first section and a straight wall engaging section extending angularly from said elbow toward said trailing end.

9. The blood clot filter of claim 8 wherein said straight wall engaging section is shorter in length than said elongate substantially straight first section.

10. The blood clot filter of claim 9 wherein said elongate legs are of greater length than said elongate arms.

11. The blood clot filter of claim 10 wherein said straight wall engaging section is no more than one fourth the length of said elongate, substantially straight first section.

12. The blood clot filter of claim 1 wherein each wire of said first and second plurality of spaced wires includes a contact end for contacting the wall of said blood vessel in the expanded configuration of said blood clot filter and a substantially straight wire section extending from said contact end, said straight wire section extending at an angle of less than 45 degrees to the blood vessel wall when said contact end is in contact with said blood vessel wall.

13. The blood clot filter of claim 1, wherein said second filter basket is spaced from said first filter basket.

14. The blood clot filter of claim 13 wherein said elongate legs are straight and are longer than said elongate arms.

15. A method for removing a blood clot filter having a leading end and a trailing end from engagement with the walls of a vessel, the blood clot filter having a longitudinal axis, a first plurality of elongate arms curving outwardly away from the longitudinal axis toward said trailing end to form a first filter basket, and a second plurality of elongate legs angling outwardly away from said longitudinal axis toward the leading end to form a second filter basket, the method including the steps of:

holding the filter against longitudinal movement while moving the arms thereof toward the leading end of the filter to disengage the arms from engagement with the vessel walls, and subsequently moving the filter longitudinally in the direction of the trailing end thereof to withdraw the elongate legs from engagement with the vessel wall.

16. The method of claim 15 which includes moving a removal tube over the trailing end of the filter into engagement with the elongate arms and then toward the filter leading end for a distance sufficient to disengage the arms from the vessel wall without engaging the removal tool with the elongate legs.

17. The method of claim 16 which includes holding said removal tube in position after disengaging said elongate arms from the vessel wall and drawing said filter into said removal tube to withdraw the elongate legs from engagement with the vessel wall.

18. A blood clot filter having a central longitudinal axis which is collapsible into a collapsed configuration toward said longitudinal axis for insertion into a blood vessel and which is radially expansible outwardly from said longitudinal axis to an expanded configuration for contact with an inner wall of said blood vessel at two longitudinally spaced locations, said blood clot filter having leading and trailing ends and comprising:

a first plurality of spaced wires which, in the expanded configuration of said filter extend angularly outward away from said longitudinal axis toward the leading edge of the blood clot filter and then bend at an elbow to extend angularly toward the trailing end of said blood clot filter to form a first filter basket and a second plurality of spaced wires which, in the expanded configuration of said filter angle outwardly away from said longitudinal axis toward the leading end of said blood clot filter to form a second filter basket opening toward said leading end.

19. The blood clot filter of claim 18 wherein said first filter basket opens toward said trailing end.

* * * * *